US009675369B2

(12) United States Patent
Teague et al.

(10) Patent No.: US 9,675,369 B2
(45) Date of Patent: Jun. 13, 2017

(54) MULTI-FUNCTIONAL MEDICAL DEVICE

(75) Inventors: James A. Teague, Spencer, IN (US); Eric Cheng, New Richmond, OH (US); Mohamed Fazni Aziz, Bloomington, IN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1960 days.

(21) Appl. No.: 12/314,749

(22) Filed: Dec. 16, 2008

(65) Prior Publication Data

US 2009/0157060 A1 Jun. 18, 2009

Related U.S. Application Data

(60) Provisional application No. 61/006,084, filed on Dec. 18, 2007.

(51) Int. Cl.
*A61B 17/00* (2006.01)
*A61B 17/221* (2006.01)
*A61B 17/29* (2006.01)

(52) U.S. Cl.
CPC .. *A61B 17/221* (2013.01); *A61B 2017/00336* (2013.01); *A61B 2017/00424* (2013.01); *A61B 2017/2923* (2013.01)

(58) Field of Classification Search
CPC ................................. A61B 17/2909
See application file for complete search history.

(56) References Cited

U.S. PATENT DOCUMENTS

| 4,750,475 | A | 6/1988 | Yoshihashi |
| 5,462,527 | A | 10/1995 | Stevens-Wright et al. |
| 5,626,608 | A | 5/1997 | Cuny et al. |
| 5,766,184 | A | 6/1998 | Matsuno et al. |
| 5,817,104 | A | 10/1998 | Bilitz et al. |
| 6,235,026 | B1 * | 5/2001 | Smith ............................ 606/46 |
| 6,258,101 | B1 | 7/2001 | Blake |
| 6,267,759 | B1 | 7/2001 | Quick |
| 6,419,679 | B1 | 7/2002 | Dhindsa |
| 6,494,885 | B1 | 12/2002 | Dhindsa |
| 6,551,327 | B1 | 4/2003 | Dhindsa |

(Continued)

FOREIGN PATENT DOCUMENTS

WO WO 2007/109070 A 9/2007

OTHER PUBLICATIONS

International Search Report from the European Patent Office for the corresponding PCT application No. PCT/US2008/087000 (8 pages).

*Primary Examiner* — Lynsey Crandall
(74) *Attorney, Agent, or Firm* — Bookoff McAndrews, PLLC

(57) ABSTRACT

An embodiment of a medical device includes a proximal handle, a distal end effector, an elongate member connecting the end effector to the handle, and a sheath enclosing at least a portion of the elongate member. The handle may include a first mechanism coupled to one of the sheath and the elongate member to move the sheath relative to the elongate member, a second mechanism coupled to the elongate member to rotate the elongate member relative to the handle, and a locking mechanism coupled to the first mechanism to hold the first mechanism in a default position. Embodiments also include methods of positioning the medical device to perform a medical procedure.

19 Claims, 5 Drawing Sheets

(56) References Cited

U.S. PATENT DOCUMENTS

| | | |
|---|---|---|
| 6,554,843 B1 | 4/2003 | Ou |
| 6,652,537 B2 | 11/2003 | Mercereau et al. |
| 6,676,668 B2 | 1/2004 | Mercereau et al. |
| 6,709,667 B1 * | 3/2004 | Lowe et al. ................. 424/422 |
| 6,743,237 B2 | 6/2004 | Dhindsa |
| 6,764,499 B2 | 7/2004 | Honey et al. |
| 6,976,955 B2 | 12/2005 | Hardin et al. |
| 7,087,062 B2 | 8/2006 | Dhindsa |
| 7,300,438 B2 | 11/2007 | Falwell et al. |
| 7,331,958 B2 | 2/2008 | Falwell et al. |
| 2003/0009176 A1 | 1/2003 | Bilitz |
| 2003/0023247 A1 | 1/2003 | Lind et al. |
| 2003/0036712 A1 | 2/2003 | Heh et al. |
| 2003/0181876 A1 | 9/2003 | Ahn et al. |
| 2003/0236493 A1 | 12/2003 | Mauch |
| 2004/0082880 A1 | 4/2004 | Heh et al. |
| 2004/0097964 A1 | 5/2004 | Dhindsa |
| 2004/0127847 A1 | 7/2004 | DuBois et al. |
| 2004/0133213 A1 | 7/2004 | Bagley et al. |
| 2004/0147828 A1 | 7/2004 | Gibson |
| 2004/0181140 A1 | 9/2004 | Falwell et al. |
| 2005/0065467 A1 | 3/2005 | Pudelko et al. |
| 2005/0096590 A1 | 5/2005 | Gullickson et al. |
| 2005/0143774 A1 | 6/2005 | Polo |
| 2005/0245847 A1 | 11/2005 | Schaeffer |
| 2005/0267327 A1 | 12/2005 | Iizuka et al. |
| 2005/0288551 A1 * | 12/2005 | Callister ............ A61B 1/00082 600/115 |
| 2006/0004376 A1 | 1/2006 | Shipp et al. |
| 2006/0069399 A1 | 3/2006 | Weisel et al. |
| 2006/0116692 A1 | 6/2006 | Ward |
| 2006/0173468 A1 | 8/2006 | Simmon et al. |
| 2006/0195140 A1 | 8/2006 | Banju et al. |
| 2006/0235431 A1 | 10/2006 | Goode et al. |
| 2006/0252993 A1 | 11/2006 | Freed et al. |
| 2006/0265007 A1 | 11/2006 | White et al. |
| 2007/0093790 A1 | 4/2007 | Downey et al. |
| 2007/0112409 A1 | 5/2007 | Wu et al. |
| 2007/0191674 A1 | 8/2007 | Zirps et al. |
| 2007/0191865 A1 | 8/2007 | Pappas |
| 2007/0219550 A1 | 9/2007 | Thompson et al. |
| 2007/0255289 A1 | 11/2007 | Nakao |
| 2007/0260264 A1 | 11/2007 | Nobis et al. |
| 2007/0282358 A1 | 12/2007 | Remiszewski et al. |
| 2007/0287993 A1 * | 12/2007 | Hinman et al. ................... 606/1 |
| 2010/0268189 A1 * | 10/2010 | Byrnes et al. ................ 604/506 |

* cited by examiner

MULTI-FUNCTIONAL MEDICAL DEVICE

CROSS REFERENCE TO RELATED APPLICATIONS

This application is based upon and claims the benefit of priority under 35 U.S.C. §119(e) of U.S. Provisional Application No. 61/006,084 to Teague et al. filed on Dec. 18, 2007.

FIELD OF THE INVENTION

Embodiments of this invention relate to handle assemblies for medical devices for medical treatment, including, for example, immobilization, capture, repositioning, and fragmentation of objects within the anatomical lumens of the body. More particularly, embodiments of the invention relate to improved medical handles for performing a number of functions with a single hand of an operator.

BACKGROUND OF THE INVENTION

Medical devices having elongated body portions can be introduced through a body opening or tract and manipulated to move material (e.g., blood clots, tissue, biological concretions, medical device components) within the body. Using such devices positioned at a treatment site through an elongated endoscope, laparoscope, or ureteroscope, an operator can view and operate simultaneously at a remote surgical site. Lithotripsy and ureteroscopy, for example, are used to treat urinary calculi (e.g., kidney stones) in the ureter of a patient. In ureteroscopy, an operator inserts a medical retrieval device such as a surgical grasper or a metal wire basket into the urinary tract to capture a stone in the retrieval assembly. Holding the stone in position within the retrieval assembly, the operator fragments it using a laser fiber. The operator can then remove the fragments by the same or a different medical retrieval device or leave them in the body to be eliminated naturally.

Medical retrieval devices can include a sheath and an object-engaging unit, such as a basket, that is moveable relative to the sheath from a collapsed state within the sheath to another state in which the unit extends past the distal end of the sheath. The sheath typically extends from a handle, located at the proximal end (i.e., the end away from the patient) of the sheath to the object-engaging unit which is located at the distal end of the sheath (i.e., the end near the patient and that goes into the patient). The handle includes a mechanism for actuating the object-engaging unit in order to move the object-engaging unit between collapsed and extended, expanded states.

During a urological procedure, a physician should be able to move the distal end of the medical retrieval device in relation to the distal end of a ureteroscope. The physician may grip the sheath just proximal to the point where the sheath is introduced into an auxiliary channel within the ureteroscope. As the physician operates the ureteroscope and positions the sheath of the retrieval device, an assistant actuates the handle at the physician's direction to retrieve or manipulate foreign material.

In procedures that utilize a laser fiber and retrieval device, the physician must carefully hold and position both items relative to each other as well as relative to the ureteroscope. Actuation of the devices with the assistance of another operator can be overly time consuming, cumbersome, and lacking in tactile sensitivity. Currently, operators use at least two hands to manipulate urinary calculi and fragments thereof. To retain the object(s) or hold the retrieval device in a certain position and location, the operator should maintain constant tension on the handle. To rotate or move the device, the operator should maintain that tension while rotating the handle, often requiring another operator. There exists a need for a locking mechanism that allows a physician to release tension on the handle without changing the tension of the device on the captured object. Currently, physicians who need to maintain a certain position of the basket in the process of manipulating a stone must employ an attending assistant to actuate the device, which adds cost and separates the physician from the tactile feel of the device.

Retrieval of fragments of urinary calculi within the body can be problematic in that stones or stone fragments in the ureter often migrate within the body before, during, and after a lithotripsy procedure. Therefore, a need exists in the art for a retrieval device that facilitates the initial capture of material as well as maintaining its capture during further positioning and removal of the material and device. In addition, there exists a need in the art for a retrieval device that facilitates the controlled release of a stone or fragment during a surgical procedure. For example repositioning a target stone relative to a lithotripter or releasing captured stones to large to release without fragmentation requires controlled release of material.

Operators of medical retrieval devices need an improved handle that allows for the introduction, positioning, and actuation of the device with a single hand. An improved handle would allow an operator to simultaneously position and manipulate two devices relative to each other. Additionally, using an improved handle, an operator could simultaneously manipulate an endoscope or an additional medical device without assistance. Improved configurations for those devices should exhibit improved capabilities for sustained capture, controlled release, and limited patient tissue trauma while allowing operation of the devices without the need for two hands or an assistant. There is also a need for smaller handles that have more ability to manipulate objects so that the primary operator has the highest possible tactile sensation of and control over the object to be captured or manipulated.

SUMMARY OF THE INVENTION

Embodiments of this invention relate to handle assemblies for medical devices for medical treatment, including, for example, immobilization, capture, repositioning, and fragmentation of objects within the anatomical lumens of the body.

In one embodiment, the medical device includes a proximal handle, a distal end effector, an elongate member connecting the end effector to the handle, and a sheath enclosing at least a portion of the elongate member. The handle has a first mechanism coupled to one of the sheath and the elongate member to move the sheath relative to the elongate member, and a second mechanism coupled to the elongate member to rotate the elongate member relative to the handle.

In various embodiments, the device may include one or more of the following additional features: wherein the first mechanism is a rotatable piece that engages a longitudinally moveable piece fixedly attached to one of the sheath and the elongate member; wherein the rotatable piece is a first gear and the longitudinally moveable piece is a second gear; wherein a filled tooth of at least one of the first and second gears restricts the movement of the first mechanism; wherein the rotatable piece is positioned for actuation by a thumb or finger of one hand of a user; wherein the second mechanism is positioned for actuation by a thumb or finger of the one hand, other than the thumb or finger for actuation of the rotatable piece; wherein the rotatable piece rotates along an axis perpendicular to a longitudinal axis of the device; wherein the second mechanism is a knob that rotates about a longitudinal axis of the handle; wherein the second mechanism engages a mechanism that fixedly retains the elongate member; wherein the knob is at least partially exposed on the handle; wherein the mechanism that fixedly retains the elongate member is one of a pinch vise, a clip, a staple, and a clamp; further comprising a locking mechanism coupled to the first mechanism to hold the first mechanism in a default position; further comprising a biasing member coupled to the first mechanism to hold the first mechanism in a default position.

Another embodiment of the invention is directed to a medical device including a proximal handle, a distal end effector, an elongate member connecting the end effector to the handle, and a sheath enclosing at least a portion of the elongate member. The handle includes a first mechanism coupled to one of the sheath and the elongate member to move the sheath relative to the elongate member, and a locking mechanism coupled to the first mechanism to hold the first mechanism in a default position.

In various embodiments, the medical device may include one or more of the following additional features: wherein the locking mechanism comprises a gear portion connected to the first mechanism that, in the default position, engages a lug of the handle; wherein the gear, in a depressed position, disengages from the lug and allows movement of the first mechanism; wherein teeth of the gear engage teeth of the lug wherein the locking mechanism comprises one or more springs biasing the first mechanism toward the default position, wherein the springs comprise two springs; wherein the first mechanism includes a rotatable piece, and the one or more springs restrict rotation of the rotatable piece Another embodiment of the invention is directed to a method of positioning a medical device to perform a medical procedure including providing the medical device including a proximal handle, a distal end effector, an elongate member connecting the end effector to the handle, and a sheath enclosing at least a portion of the elongate member; with the distal end effector within the sheath, advancing the distal end effector proximate to a treatment site within a body lumen of a patient; actuating a first mechanism of the handle with a thumb or finger of a hand of an operator to expose the end effector from the sheath; and actuating a second mechanism of the handle with a thumb or a finger of the hand of the operator to rotate the end effector about a longitudinal axis of the device and relative to the handle.

In various embodiments, the method may include one or more of the following additional features: wherein actuating the first mechanism comprises turning a rotatable piece, the rotatable piece engaging a longitudinally moveable piece attached to one of the sheath and the elongate member; wherein the thumb or finger rotates the rotatable piece about an axis perpendicular to a longitudinal axis of the handle; wherein the hand of the operator actuates the first mechanism and thereafter actuates the second mechanism without the operator repositioning the hand on the handle; wherein actuating the second mechanism comprises rotating a knob that is fixedly attached to the elongate member; wherein the thumb actuates the first mechanism and a finger actuates the second mechanism without the operator repositioning the hand on the handle; wherein depressing the rotatable piece releases the first mechanism from a default position; wherein releasing the rotatable piece places the first mechanism in a default position; wherein the end effector expand when exposed from the sheath; wherein actuating the second mechanism occurs after actuating the second mechanism.

Another embodiment of the invention is directed to a method of positioning a medical device to perform a medical procedure, including providing the medical device including a proximal handle, a distal end effector, an elongate member connecting the end effector to the handle, and a sheath enclosing at least a portion of the elongate member; with the distal end effector within the sheath, advancing the distal end effector proximate to a treatment site within a body lumen of a patient; actuating a first mechanism of the handle with a thumb or finger of a hand of an operator to expose the end effector from the sheath; and locking the end effector in a longitudinal position relative to the sheath.

In various embodiments, the method may include one or more of the following additional features: wherein actuating the first mechanism comprises turning a rotatable piece, the rotatable piece engaging a longitudinally moveable piece attached to one of the sheath and the elongate member; wherein the thumb or finger rotates the rotatable piece about an axis perpendicular to a longitudinal axis of the handle; further including actuating a second mechanism of the handle with a thumb or a finger of the hand of the operator to rotate the end effector about a longitudinal axis of the device and relative to the handle; wherein locking the end effector comprises releasing the first mechanism from actuation; further including unlocking the end effector from a longitudinal position relative to the sheath via actuation of the first mechanism; wherein unlocking the end effector comprises depressing the first mechanism from a default position; wherein the first mechanism is depressed against a biasing force.

BRIEF DESCRIPTION OF THE DRAWINGS

The accompanying drawings, which are incorporated in and constitute a part of this specification, illustrate several embodiments of the invention and together with the description, serve to explain the principles of the invention.

DESCRIPTION OF THE EMBODIMENTS

Figure 1:
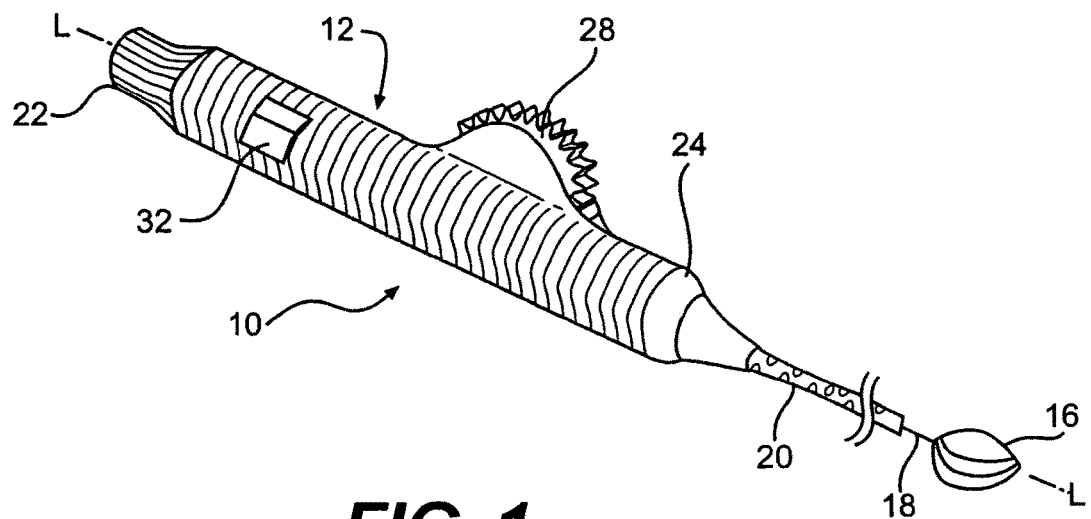
FIG. 1 illustrates a perspective view of a medical retrieval device according to an embodiment of the invention.

Reference will now be made in detail to the exemplary embodiments of the invention, examples of which are illustrated in the accompanying drawings. Wherever possible, the same reference numbers will be used throughout the drawings to refer to the same or like parts.

FIGS. 1-8 illustrate a first embodiment of a medical device according to the invention. The medical device 10 includes a handle 12, a sheath 20, an elongate member 18, and an end effector 16. Sheath 20 may be flexible and includes an internal lumen for receiving the elongate member 18 and the end effector 16. As will be described more in detail below, the end effector 16 and sheath 20 are moveable relative to each other in order to achieve a first collapsed state of the end effector 16 (not shown) in which the end effector 16 is collapsed within the lumen of the distal end of the sheath 20 and a second state in which the end effector 16 extends from the distal end of the sheath 20 and expands (shown in FIG. 1).

The sheath 20 defines a lumen dimensioned to fully enclose the elongate member 18 and the end effector 16 when the end effector 16 is in the retracted position (not shown). The sheath 20 extends from the distal end 24 of the handle 12 to the end effector 16. When extended past the proximal end of the end effector 16, the sheath 20 envelopes the end effector 16, placing the end effector 16 in a collapsed state. When the sheath 20 moves proximally relative to the end effector 16, it exposes the end effector 16 and leaves it in an expanded state (shown in FIG. 1).

The sheath 20 may be formed from various biocompatible materials or combination of biocompatible materials known in the art. Such materials may include, but are not limited to, polyamide, PEBAX, stainless steel (such as 300 and 400 series), cobalt, chromium, nickel, titanium, nitinol, thermoforming plastic, polytetrafluoroethylene ("PTFE"), and expanded polytetrafluoroethylene ("ePTFE"). The sheath 20 may also be a metal coated with a polymer and may have one or more layers of material. Additionally, any of the materials discussed below or combination thereof with respect to the elongate member 18 may form the sheath 20.

The length and diameter of the sheath 20 may vary depending on the application. A relatively long sheath 20 may be advantageous for retrieving stones or other calculi deep within the body of the patient. A sheath 20 having a relatively small diameter may be advantageous for retrieving stones from restricted passageways within the human urinary tract. The sheath 20 may be relatively flexible to facilitate the retrieval of stones or other material located in complex, tortuous body structures.

An elongate member 18 lies partially within the sheath 20. Elongate member 18 is preferably a wire formed of a biocompatible material such as stainless steel, cobalt, chromium, nickel, titanium, nitinol, or other suitable metal. The member 18 may be in the form of a flexible shaft, coil, cable, or wire.

The elongate member 18 extends proximally from the end effector 16 into the handle body 12. In one configuration, the proximal end of the elongate member 18 is connected to a movable internal portion of the handle 12, such that movement of the internal portion will move the end effector 16 relative to sheath 20 between expanded and collapsed states. In another configuration not shown, the proximal end of the sheath 20 may connect to a movable internal portion of the handle body 12, such that movement of the movable internal portion will extend the sheath 20 over the end effector 16 and thereby collapse the end effector 16.

The end effector 16 may comprise a basket, grasper, snare, claw, or any other retrieval or grasping mechanism. The end effector 16 may also comprise any other mechanism for performing an operation in a body and may be suitable for urological, endoscopic, or other like procedures.

FIG. 1 shows an embodiment having an end effector in the form of a basket having a plurality of moveable legs. The basket collapses into a closed position when the elongate member 18 moves proximally relative into the sheath 20. When the basket moves distally relative to and out of the sheath 20, the basket expands to an open, unfurled, or spread out position.

The proximal end of the elongate member 18 extends into the handle 12. Handle 12 and sheath 20 and elongate member 18 extend along the same longitudinal axis L-L of the device, as shown in FIG. 1. Handle 12 includes an elongated handle body, including a proximal handle end 22 (farthest away from the patient) and a distal handle end 24. End effector 16 extends distally from elongate member 18 disposed within the lumen of the sheath 20. The elongate member 18 extends proximally from the end effector 16 into the handle 12. In this embodiment, the proximal end of the elongate member 18 is connected to an internal portion of the proximal end of the handle 12, but the elongate member 18 may extend to any part of the handle 12 between the distal end 24 and the proximal end 22.

Figure 3:
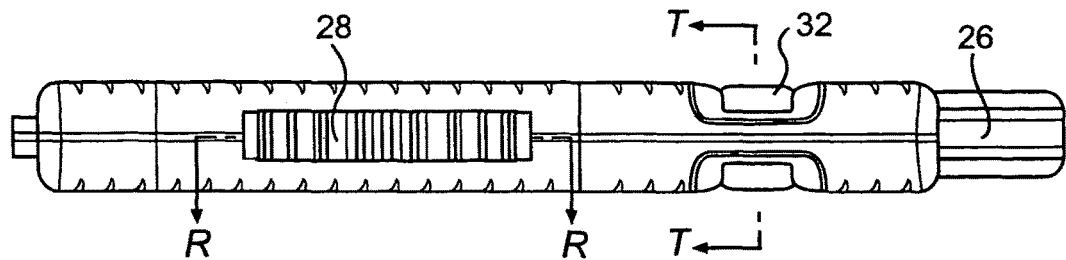
FIG. 3 is a top view of the embodiment of FIG. 1.
Figure 4:
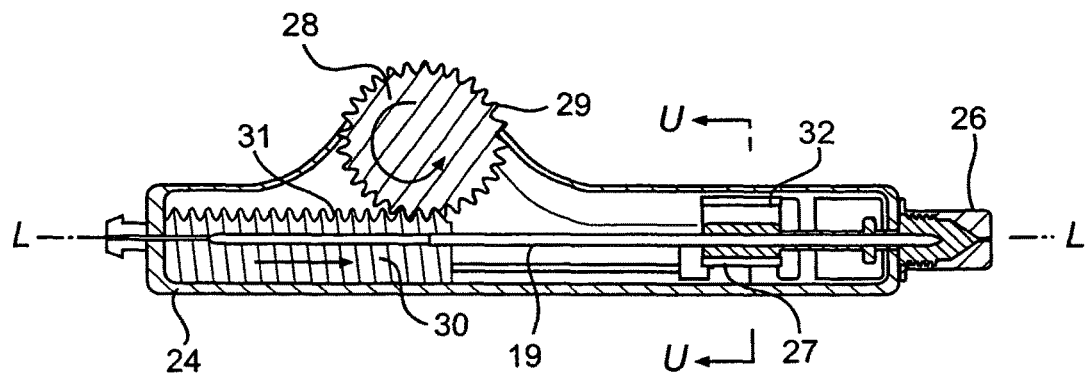
FIG. 4 is a detailed side cross-sectional view of the medical retrieval device of FIG. 1, along line A-A of FIG. 2.
Figure 5:
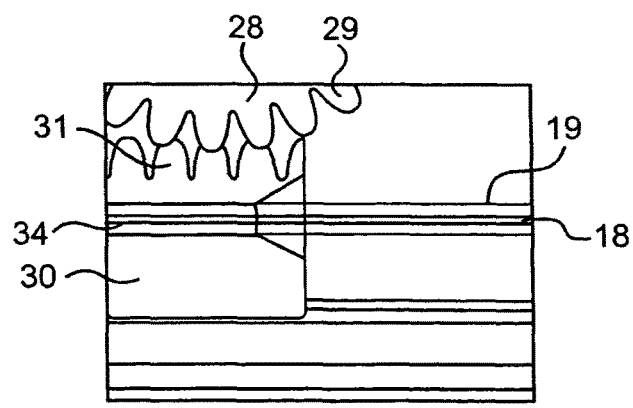
FIG. 5 is a detailed view of the rack gear and telescoping cannula.

Handle 12 further includes a thumb wheel 28, configured to lie where the thumb is located when a hand grips the device 10, and a rotation knob 32, configured to lie where a finger is located on the device 10. Handle 12 is gripped in the palm of a hand. With a single hand, an operator can grip the handle 12, turn the thumb wheel 28, and actuate the rotation knob 32. As shown in FIGS. 3 and 4, the thumb wheel 28 rotates about an axis perpendicular to the longitudinal axis L-L of the handle 12; and the rotation knob 32 rotates about an axis parallel to axis L-L.

A thumb or finger turns the thumb wheel 28 to extend and retract the sheath 20 along its longitudinal axis. The thumb wheel 28 is a disc or gear with teeth or ridges 29 along its circumference. Most of the thumb wheel 28 lies within the handle 12 between the middle and the distal end 24 of the handle 12. Part of the wheel 28 is exposed to allow the operator to grip the edge of wheel 28 with a thumb or finger to turn the wheel 28. The thumb wheel teeth 29 improve finger or thumb grip on the wheel 28 and engage the teeth 31 on a rack gear 30. Other textured or rough surfaces may line the circumference of thumb wheel 28 so that the wheel 28 can engage rack gear 30.

The thumb wheel 28 is held in a default position by a biasing system, such as one or more springs that hold the thumb wheel teeth 29 in place so they will not engage the rack gear teeth 31 when the thumb wheel 28 is in the default position. When the thumb wheel 28 is depressed, the biasing system (not shown) yields and the thumb wheel teeth 29 engage the rack gear teeth 31.

Figure 7:
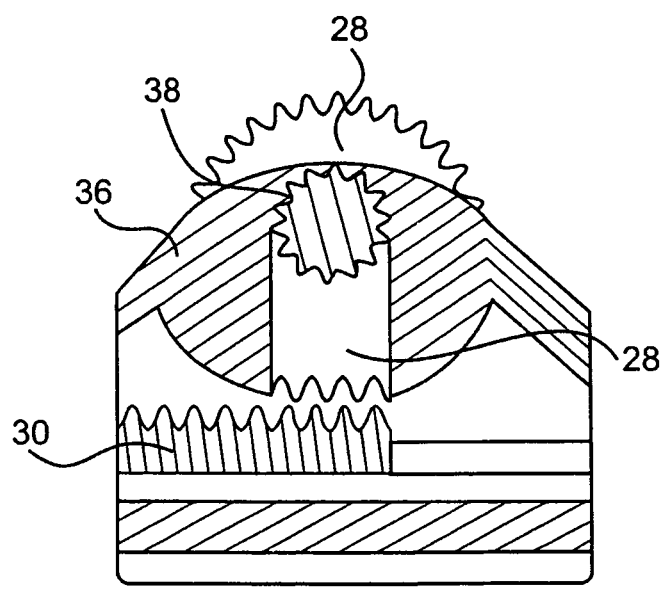
FIG. 7 is a cross-sectional view, along line R-R of FIG. 3, showing an embodiment of the invention.

The handle 12 includes a locking mechanism to lock the thumb wheel 28 in place when not depressed. As shown in FIG. 7, in this embodiment, the locking mechanism includes a locking piece 36 and an inner gear 38. Inner gear 38 attached to the thumb wheel 28 within the handle 12 is positioned under locking piece 36. The locking piece 36 attaches to or is otherwise an integral portion of the body of the handle 12. When the thumb wheel 28 is not depressed, teeth on the top of the outer edge of the inner gear 38 engage teeth or any textured surface on the inside of the locking piece 36 where it meets the inner gear 38 to hold the inner gear 38 in place. In turn, the inner gear 38 holds the thumb gear 28 in place and keeps it from rotating. When depressing or lowering the thumb wheel 28 toward the central axis L-L of the handle 12, thereby also depressing gear 38, the operator releases the teeth of the inner gear 38 from the locking piece 36, enabling the thumb wheel 28 to turn and the rack gear 30 and the sheath 20 to move along the L-L axis. By releasing the thumb wheel 28 and permitting wheel 28 to raise to a default position, the operator causes the teeth of the inner gear 38 to engage the locking piece 36, which locks the thumb wheel 28 and the rack gear 30 in place once again.

In this embodiment, the operator activates mechanisms on the handle to move the sheath 20 toward the distal end of the device 10 relative to elongate member 18 by turning the top of the thumb wheel 28 toward the proximal end of the handle 22; or clockwise in FIG. 4. This will cause the end effector 16 to collapse into the sheath 20. By turning the top of the thumb wheel 28 toward the distal end of the handle 24, or counter-clockwise in FIG. 4, the operator moves the rack gear 30 and sheath 20 toward the proximal end of the device 10, exposing the end effector 16 for expansion.

The rack gear 30 includes a long element or rack that lies within the handle 12. The long element of the rack gear 30 is connected to the sheath 20 and is configured to move along the longitudinal axis L-L of the handle 12. Teeth 29 on the edges of thumb wheel 28 engage or interfit with teeth 31 on the long element of the rack gear 30, thereby causing movement of the rack gear when the thumb wheel 28 turns.

Engaging thumb wheel 28 telescopes a stiffening cannula 19 into rack gear 30 and sheath 20, providing the required support to push and pull gear 30 over the elongate member 18 without need for and additional, overlapping cannula. Telescoping cannula 34 prevents existing cannula 19 from protruding into the proximal end of the sheath 20, common in prior handles. The sheath 20 extends into at least the distal end of a lumen of rack gear 30 and fixedly connects to rack gear 30.

In other embodiments, the thumb wheel may utilize a toggle lock or any other locking system to keep the wheel from moving inadvertently. Other embodiments may also place the thumb wheel in a position for actuation by a finger instead of a thumb. The rack gear system may be configured such that turning the thumb wheel toward the proximal end of the handle moves the rack gear and sheath toward the proximal end of the handle. The system may also be configured to restrict the thumb wheel and rack gear to certain positions or favor certain positions over others by altering the design of the surface of the thumb wheel or the surface of the rack gear.

Movement of the rack gear 30 along longitudinal axis L-L causes movement of sheath 20 along the same axis, in the same direction. The movement of the sheath 20 relative to the elongate member 18 along the L-L axis in the direction of the end effector 16 eventually situates the end effector 16 in its collapsed state, not shown here. Movement of the sheath 20 in the direction of the proximal end of the handle 12 eventually situates the end effector 16 in its expanded or unfurled state.

As shown in the FIGS. 1-4 and 6, this embodiment of the handle 12 comprises a rotation knob 32 positioned between the proximal end 22 of the handle 12 and the thumb wheel 28. The rotation knob 32 lies within the handle 12 except for a part exposed through an opening in the handle 12 through which the operator can actuate the knob 32. The opening is large enough so that an operator of the device 10 may move the knob 32 with a slight downward or upward motion of a finger (relative to the position of the device shown in, for example, FIGS. 1 and 4). In another embodiment, the system may be configured so that the rotation knob is actuated by a forward or backward motion of a finger.

Figure 6:
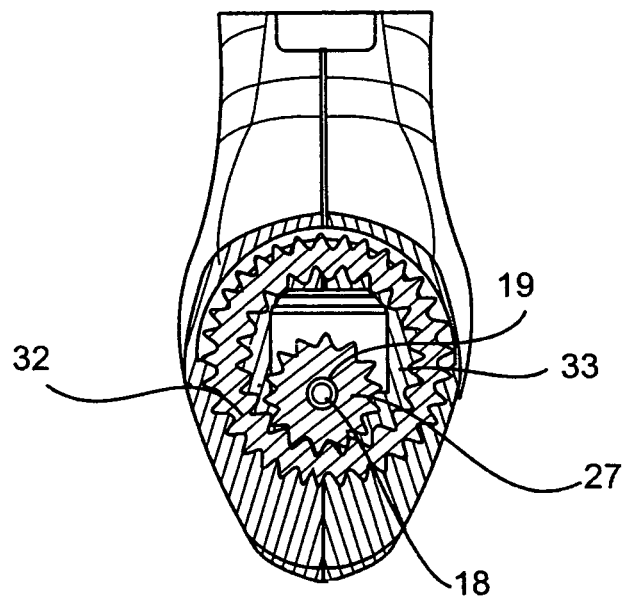
FIG. 6 is a cross-sectional view of the rotation knob connected to the pinch vise and mandril wire spindle along line T-T of FIG. 3 and line U-U of FIG. 4, according to an embodiment of the invention.

As shown in detail in the cross-sectional view of FIG. 6 (which is a view along axis U-U of FIG. 4), the knob 32 is shaped as a hollow cylinder whose longitudinal axis lies substantially along, or parallel to, the longitudinal axis L-L of the handle 12. Teeth or ridges surround the outer edges of knob 32, allowing a single finger to turn the knob 32. The interior of knob 32 includes gear teeth. Those gear teeth interfit with the teeth lining the outer edge of a portion of a pinch vise 27, located at the proximal end 22 of the handle 12. The pinch vise 27 grips stiffening cannula 19 and elongate member 18. When the operator turns the rotation knob 32, the gear system rotates the pinch vise 27, and the torque of the pinch vise 27 turns the elongate member 18 about its longitudinal axis. When the elongate member 18 rotates about its longitudinal axis, the end effector 16, attached to the distal end of the elongate member 18, also rotates about its longitudinal axis.

By turning the right edge of the rotation knob toward the bottom of the device, or clockwise in FIG. 6, the operator will rotate the end effector 16 clockwise. By turning the right edge of the rotation knob toward the top of the device, or counter-clockwise in FIG. 6, the operator will rotate the end effector 16 counter-clockwise.

Other embodiments may place the rotation knob where it could be operated by a thumb or another part of the hand instead of a finger.

Using the thumb wheel 28 and the rotation knob 32 on the handle 12 of this embodiment of the medical device 10, a physician can manipulate or position the sheath 20 relative to the end effector with a single hand by rolling the thumb wheel 28 with a thumb or finger, thereby moving the sheath 20 proximally or distally; and by actuating the rotation knob 32 with a different finger, thereby rotating the elongate member 18 and the end effector 16 about their longitudinal axes.

Figure 2:
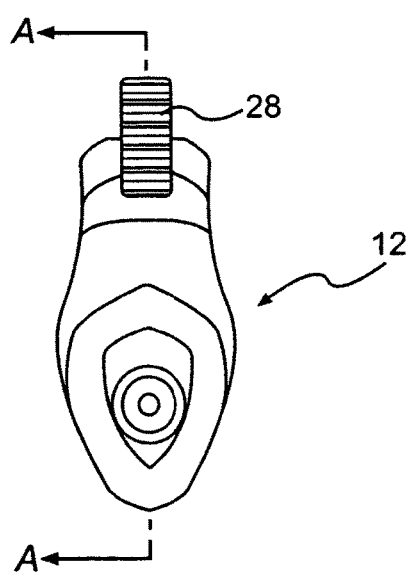
FIG. 2 is a view from the distal end of the embodiment of FIG. 1.
Figure 8:
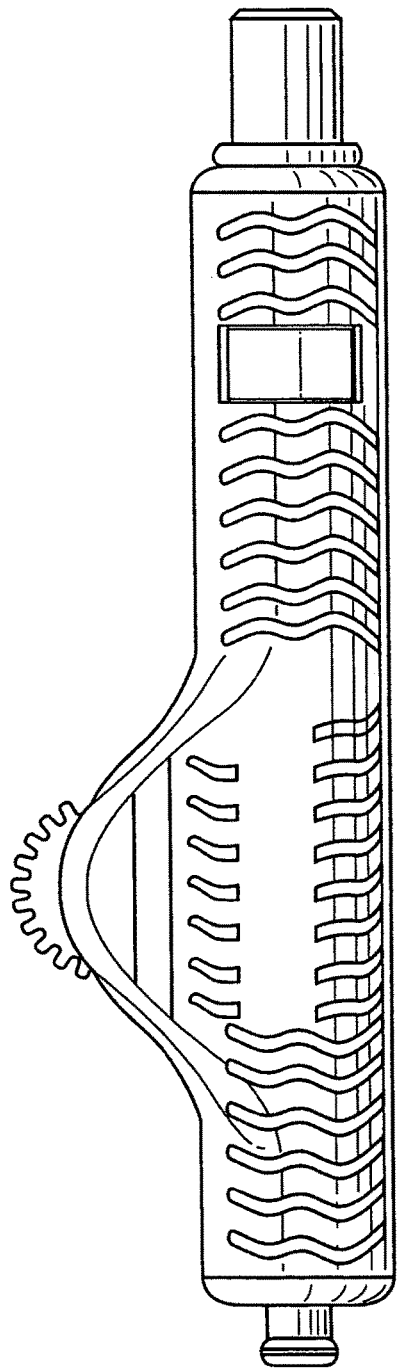
FIG. 8 is a side view of the embodiment of the invention show in FIG. 1.
Figure 10A:
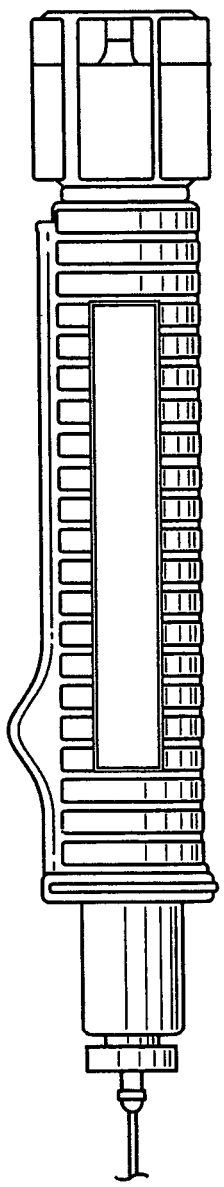
FIG. 10A is a side view of a current handle in the art.
Figure 10B:
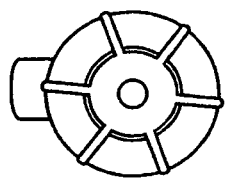
FIG. 10B is a view from the distal end of the handle of FIG. 10A.

Embodiments of invention enables medical devices whose handles are lighter and smaller than current handles in the art. FIGS. 8 and 2 show the shapes and dimension of the embodiment of FIG. 1 relative to those of current handles in the art, shown in FIGS. 10A and 10B. As shown by FIG. 2 as compared to FIG. 10B, the handle in the embodiment of FIG. 1 is slimmer than the cross-section of current handles in the art. As shown by the side view of FIG. 8 as compared to FIG. 10A, the handle of the embodiment of FIG. 1 is shorter and thinner than current handles. As a result, the handle in the embodiment of FIG. 1 weighs less than current handles.

Figure 9:
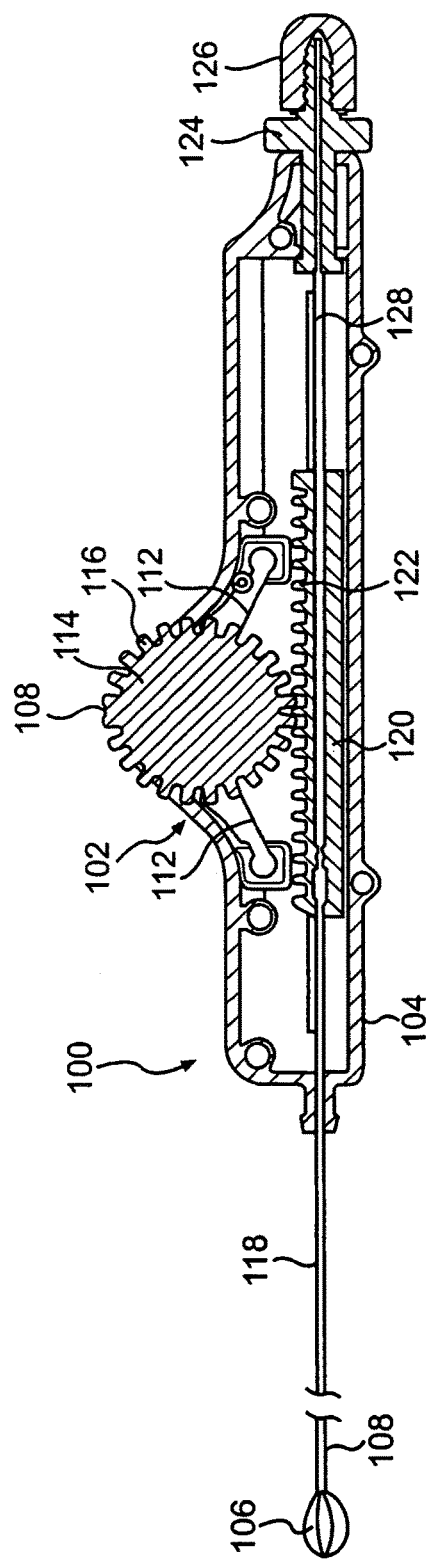
FIG. 9 is a cross-sectional side view of a second embodiment of a medical retrieval device according to the invention.

FIG. 9 illustrates another embodiment of a medical device according to the invention. The FIG. 9 embodiment is similar in many respects to the embodiment shown in FIGS. 1-8.

The medical device 100 includes a handle 102, a sheath 118, an elongate member 110, and an end effector 106. Sheath 118 may be flexible and includes an internal lumen for receiving the distal end effector 106 at the distal end of member 110. The end effector 106 and sheath 118 are moveable relative to each other in order to achieve a first collapsed state of the end effector 106 in which the end effector 106 is collapsed within the lumen of the distal end of the sheath 118 and a second state in which the end effector 106 extends from the distal end of the sheath 118 and expands. The end effector 106 may comprise any of the mechanisms described in the description of the end effector of the embodiment above.

Handle 102 of medical device 100, sheath 118, and elongate member 110 extend along the same longitudinal axis L-L. Handle 102 includes an elongated handle body, including a proximal handle end 130 and a distal handle end 104. The end effector 106 extends distally from elongate member 110 disposed within the lumen of the sheath 118. The elongate member 110 extends proximally from the end effector 106 into the handle 102 and may be in the form of a flexible shaft, coil, cable, or wire. In this embodiment, the proximal end of the elongate member 110 is connected to the proximal end 130 of the handle 102.

Handle 102 further includes a thumb gear 114 with teeth 116, the exposed portion of the gear 114 positioned where the thumb lies when a hand grips the device 100. Handle 102 also includes a rotation knob 124, close to the proximal end of the handle and connected to a pinch vise 126. In this embodiment, the rotation knob 124 is positioned much nearer the proximal-most end of the handle 102, and closer to the outer edge of the hand gripping the handle, where the last two fingers may be best positioned to rotate the knob 124. The operator holds the handle 102 in the palm of the hand; and with a single hand, the operator can grip the handle 102, turn the thumb wheel 114, and actuate the rotation knob 124. As in the earlier embodiment, the thumb wheel 114 rotates about an axis perpendicular to the longitudinal axis of the handle 102; and the rotation knob 124 rotates about an axis parallel to the longitudinal axis of the handle 102.

In this embodiment, the thumb wheel 114 operates similarly to the thumb wheel in the embodiment above. Lever springs 112 hold the wheel 114 in a default position such that the thumb wheel teeth 116 do not engage the rack gear teeth 122 in the default position. One spring 112 exerts an upward force on a thumb wheel tooth 116, transferring torque in one direction of the thumb wheel 114. Another spring exerts an upward force on a tooth at another section of the thumb wheel 114, also transferring torque in the opposite direction of the first spring 112. As a result, the force of the springs 112 lifts the thumb wheel 114 upwards from the rack, but does not turn thumb wheel 114. This spring mechanism also acts as a locking mechanism, holding the thumb wheel in place when not depressed.

As in the embodiment of FIGS. 1-8, when the top of the thumb wheel 114 rotates toward the distal end 104 of the handle 102, thumb wheel teeth 116 engage rack gear teeth 122 and the sheath 118, attached to rack gear 120, moves toward the proximal end 130 of the device 100, exposing end effector 106. When the top of the thumb wheel 114 rotates toward the proximal end 130 of the handle 102, the sheath 118 moves to the distal end of the device 100 to cover end effector 106. By releasing the thumb wheel 114, the operator disengages the thumb wheel 114 from the rack gear 120.

FIG. 9 shows the rack gear 120 telescoping a stiffening cannula 128 as the thumb wheel teeth 116 engage the rack teeth 122. Rotating the thumb wheel 114 telescopes the stiffening cannula 128 into or out of the rack gear 120, providing the required support to push and pull the gear 120 over the elongate member 110 without the need for an additional, overlapping cannula and without the existing cannula protruding into the proximal end of the sheath 118.

As shown in FIG. 9, one or more teeth 108 in the thumb wheel 114 may be filled, which can limit throw by preventing the rack gear 120 from moving beyond a certain point when the filled tooth 108 meets the rack gear teeth 122. Filled teeth 108 can limit the distance that thumb wheel 114 rotates, which limits the distance that the thumb wheel 114 translates the rack gear 120, which in turn limits the distance that the sheath 118 can move relative to the elongate member 110. In this embodiment, the movement of the rack gear 120 is restricted in that it can not move past the point at which the filled tooth 108 engages the rack gear teeth 122. Filled teeth can be positioned at various points along the thumb wheel 108 or the rack gear 120 to limit throw.

The rack gear 120 attaches to sheath 118 inside the handle 102. Movement of the rack gear 120 along the longitudinal axis of the handle causes movement of sheath 118 along the same axis, in the same direction. Movement of the sheath 118 in the direction of the proximal end 130 of the handle 102 eventually situates the end effector 106 in its open configuration. Movement of the sheath 118 in the opposite direction toward the distal end eventually situates the end effector 106 in its collapsed position within the sheath 118.

The rotation knob 124 lies near the proximal end of the handle 102. In this embodiment, the rotation knob 124 is external to the handle body and can be actuated by a thumb or fingers at any point around the circumference of the handle 102. The rotation knob 124 is integrally formed with a pinch vise 126, and rotating the knob 124 provides torque to rotate the pinch vise 126, which rotates the stiffening cannula 128 and elongate member 110. As the pinch vise 126 rotates with the knob 124, it turns the end effector 106 about the longitudinal axis of the device in the same direction.

The configuration of medical devices 10 and 100 according to the invention allows a single user to operate an endoscope with one hand and actuate the medical device with the other hand.

The operation of devices 10 and 100 is substantially the same and will be described with reference to device 10 of FIGS. 1-8. To operate the device 10, an operator grasps the handle 12 in one hand and inserts the distal end of the device 10 into a lumen of a patient's body while the end effector 16 is in a collapsed state within the sheath 20. The operator inserts the device further into the lumen until the end effector 16 is in the proximity of the material within the lumen designated for manipulation, capture, retrieval, movement, or other diagnostic or therapeutic procedure.

When appropriate, the operator depresses the thumb wheel 28 to engage the rack gear; then, the operator turns the thumb wheel 28 on the handle 12 with the thumb of the same hand that grips the handle 12. By turning the top of the thumb wheel 28 toward the distal end of the device, the operator moves the sheath proximally relative to the elongate member 18 and the end effector 16, transitioning the end effector 16 to its expanded state. With the end effector in its expanded state, the operator can capture, contact, or manipulate the material as needed. When the target material is in range, the operator can release the thumb wheel 28, locking the position of the wheel 28 and the sheath 20. Then, if needed, the operator turns the rotation knob 32, causing the elongate member 18 and end effector 16 to rotate about the longitudinal axis L-L of the device, thereby properly positioning the end effector 16 in relation to the material. Turning knob 32 can be performed with a finger of the same hand that is holding handle 12, without repositioning that hand after turning wheel 28. Then, by depressing and turning the top of the thumb wheel 28 toward the proximal end of the device, the operator moves the sheath 20 distally in relation to the end effector 16, moving the end effector towards its collapsed state. The operator thereby grabs, envelopes, snares, or captures the material and can further manipulate it by turning the thumb wheel 28 or the rotation knob 32.

Though shown with a retrieval device (and particularly a basket), the handles described above can be used with any other medical devices which require longitudinal positioning or rotation of medical devices at a treatment site. The reference to the use of a retrieval device is used as an example and is not intended to limit the scope of the invention.

Other embodiments of the invention will be apparent to those skilled in the art from consideration of the specification and practice of the invention disclosed herein. It is intended that the specification and examples be considered as exemplary only. The following embodiments are exemplary.

We claim:

1. A medical device, comprising:
a single handle having a housing located at a proximal end of the device;
a distal end effector;
an elongate member connecting the end effector to the handle;
a sheath enclosing at least a portion of the elongate member; the single handle comprising:
a first actuator coupled to one of the sheath and the elongate member to move the sheath relative to the elongate member, wherein the first actuator is moveable along an axis perpendicular to a longitudinal axis of the sheath, the first actuator including a first rotatable member, a second rotatable member coupled to the first rotatable member, and a linear translatable member, wherein the first rotatable member extends radially outwardly of the second rotatable member relative to the longitudinal axis of the sheath, and
a second actuator coupled to the elongate member to rotate the elongate member and the end effector relative to the handle, and
wherein, in a first state, the second rotatable member is engaged with a portion of the handle housing such that the first and second rotatable members are prevented from rotating, and in a second state, the second rotatable member is disengaged from the portion of the handle housing and the first rotatable member engages the linear translatable member.

2. The device of claim 1, wherein the first rotatable member is a first gear and the linear translatable member is a second gear.

3. The device of claim 1, wherein the first rotatable member is positioned for actuation by a thumb or finger of one hand of a user.

4. The device of claim 3, wherein the second actuator is positioned for actuation by a thumb or finger of the one hand, other than the thumb or finger for actuation of the first rotatable member.

5. The device of claim 1, wherein the first rotatable member rotates along an axis perpendicular to the longitudinal axis of the sheath.

6. The device of claim 1, wherein the second actuator is a knob that rotates about the longitudinal axis of the sheath.

7. The device of claim 6, wherein the knob is at least partially exposed on the handle.

8. The device of claim 1, wherein the second actuator engages one of a pinch vise, a clip, a staple, and a clamp that fixedly retains the elongate member.

9. A method of positioning a medical device to perform a medical procedure, comprising:
with a distal end effector of a medical device positioned within a sheath of the medical device, advancing the distal end effector proximate to a treatment site within a body lumen of a patient, wherein the end effector is connected to a handle of the medical device via an elongate member positioned at least partially within the sheath;
moving a first actuator from a first state toward a second state by depressing a first rotatable member of the first actuator along an axis perpendicular to the longitudinal axis of the sheath, wherein in the first state, a second rotatable member of the first actuator is engaged with a portion of a housing of the handle, and wherein in the second state, the second rotatable member is disengaged from the portion of the handle housing and the first rotatable member engages a linear translatable member of the first actuator;
extending the end effector distally of the sheath by rotating the first rotatable member and axially advancing the linear translatable member of the first actuator with a thumb or finger of a hand of an operator; and
actuating a second actuator of the handle with a thumb or a finger of the hand of the operator to rotate the end effector about a longitudinal axis of the sheath and relative to the handle.

10. The method of claim 9, wherein the thumb or finger rotates the first rotatable member about an axis perpendicular to the longitudinal axis of the sheath.

11. The method of claim 9, wherein the hand of the operator actuates the first actuator and thereafter actuates the second actuator without the operator repositioning the hand on the handle.

12. The method of claim 9, wherein the first state includes a default position of the first actuator.

13. The method of claim 9, further including releasing the first rotatable member to return the first actuator to the first state.

14. The method of claim 9, wherein actuating the second actuator comprises rotating a knob that is fixedly attached to the elongate member.

15. The method of claim 9, further including expanding the end effector.

16. The method of claim 9, wherein actuating the second actuator occurs after actuating the first actuator.

17. A medical device, comprising:
a handle having a housing located at a proximal end of the device;
a distal end effector;
an elongate member connecting the end effector to the handle;
a sheath enclosing at least a portion of the elongate member; the handle comprising:
a first actuator coupled to one of the sheath and the elongate member to move the sheath relative to the elongate member, wherein the first actuator is moveable along an axis perpendicular to a longitudinal axis of the sheath, the first actuator including a first rotatable gear, a second rotatable gear coupled to the first rotatable gear, and a linear translatable gear, wherein the second rotatable gear is enclosed with the housing of the handle, and
a second actuator coupled to the elongate member to rotate the elongate member and the end effector relative to the handle, and
wherein, in a first state, the second rotatable gear is engaged with a portion of the handle housing such that the first and second rotatable gears are prevented from rotating, and in a second state, the second rotatable gear is disengaged from the portion of the handle housing and the first rotatable gear engages the linear translatable gear.

18. The device of claim 17, wherein the first rotatable gear is rotatable about an axis perpendicular to the longitudinal axis of the sheath.

19. The device of claim 17, wherein the second gear is a knob rotatable about the longitudinal axis of the sheath.

* * * * *